US006984250B1

(12) United States Patent
Legrand et al.

(10) Patent No.: US 6,984,250 B1
(45) Date of Patent: Jan. 10, 2006

(54) COMPOSITION, METHOD, AND KIT FOR THE BLEACHING OR PERMANENT RESHAPING OF KERATIN FIBERS, COMPRISING AT LEAST ONE THICKENING POLYMER WITH AN AMINOPLAST-ETHER SKELETON

(75) Inventors: Frédéric Legrand, Boulogne Billancourt (FR); Delphine Allard, Colombes (FR)

(73) Assignee: L'Oreal, Paris (FR)

( * ) Notice: Subject to any disclaimer, the term of this patent is extended or adjusted under 35 U.S.C. 154(b) by 522 days.

(21) Appl. No.: 10/149,008

(22) PCT Filed: Nov. 10, 2000

(86) PCT No.: PCT/FR00/03144

§ 371 (c)(1),
(2), (4) Date: Aug. 6, 2003

(87) PCT Pub. No.: WO01/41722

PCT Pub. Date: Jun. 14, 2001

(30) Foreign Application Priority Data

Dec. 8, 1999 (FR) .......................................... 99 15485

(51) Int. Cl.
*A61K 7/06* (2006.01)

(52) U.S. Cl. ........................ 8/401; 8/552; 8/602; 8/606; 8/101; 8/107; 8/110; 524/590; 525/406

(58) Field of Classification Search ...................... 8/401, 8/552, 602, 101, 107, 110; 524/590; 525/406
See application file for complete search history.

(56) References Cited

U.S. PATENT DOCUMENTS

| 2,261,002 A | 10/1941 | Ritter .......................... 260/570 |
| 2,271,378 A | 1/1942 | Searle .......................... 167/22 |
| 2,273,780 A | 2/1942 | Dittmar ........................ 260/28 |
| 2,375,853 A | 5/1945 | Kirby et al. ................. 266/588 |
| 2,388,614 A | 11/1945 | Kirby et al. ................... 167/22 |
| 2,454,547 A | 11/1948 | Bock et al. ............... 260/567.6 |
| 2,528,378 A | 10/1950 | Mannheimer ............ 260/209.6 |
| 2,781,354 A | 2/1957 | Mannheimer ............ 260/349.6 |
| 2,961,347 A | 11/1960 | Floyd .......................... 117/141 |
| 3,206,462 A | 9/1965 | McCarty .................. 260/256.4 |
| 3,227,615 A | 1/1966 | Korden ...................... 167/87.1 |
| 3,836,537 A | 9/1974 | Boerwinkle et al. ....... 260/29.6 |
| 3,874,870 A | 4/1975 | Green et al. .................... 71/67 |
| 3,929,990 A | 12/1975 | Green et al. ................... 424/78 |

(Continued)

FOREIGN PATENT DOCUMENTS

| DE | 44 38 674 | 5/1996 |
| EP | 0 080 976 | 6/1983 |
| EP | 0 122 324 | 10/1984 |
| EP | 0 337 354 | 10/1989 |
| FR | 1 400 366 | 4/1965 |
| FR | 1 492 597 | 8/1967 |
| FR | 2 077 143 | 10/1971 |
| FR | 2 080 759 | 11/1971 |
| FR | 2 190 406 | 2/1974 |
| FR | 2 252 840 | 6/1975 |
| FR | 2 270 846 | 12/1975 |
| FR | 2 316 271 | 1/1977 |
| FR | 2 320 330 | 3/1977 |
| FR | 2 336 434 | 7/1977 |
| FR | 2 368 508 | 5/1978 |
| FR | 2 383 660 | 10/1978 |
| FR | 2 393 573 | 1/1979 |
| FR | 2 413 907 | 8/1979 |
| FR | 2 470 596 | 6/1981 |
| FR | 2 505 348 | 11/1982 |
| FR | 2 519 863 | 7/1983 |
| FR | 2 542 997 | 9/1984 |
| FR | 2 598 611 | 11/1987 |
| WO | WO 99/17724 | * 4/1999 |

OTHER PUBLICATIONS

M.R. Porter, "Handbook of Surfactants," Blackie & Son, Ltd., Glasgow & London, 1991, pp. 116–178.
English language Derwent Abstract of EP 0 080 976, Jun. 8, 1983.
English language Derwent Abstract of DE 44 38 674, May 2, 1996.
English language Derwent Abstract of FR 2 077 143, Oct. 15, 1971.
English language Derwent Abstract of FR 2 080 759, Nov. 19, 1971.
English language Derwent Abstract of FR 2 320 330, Mar. 4, 1977.
English language Derwent Abstract of FR 2 336 434, Jul. 22, 1977.
Co–pending U.S. Appl. No. 10/149,073, filed Jun. 7, 2002, Delphine Allard et al., Title: Oxidation Dye Composition for Keratinic Fibres Containing a Thickening Polymer With an Ether Plastic Skeleton.
Co–pending U.S. Appl. No. 10/149,009, filed Jun. 7, 2002, Frédéric Legrand et al., Title: Composition, Process and Kit for Bleaching Keratin Fibers, Comprising at Least One Thickening Polymer With an Aminoplat–ether Skeleton.
Co–pending U.S. Appl. No. 10/148,955,—filed Jun. 7, 2002, Delphine Allard et al., Title: Direct Dyeing Composition for Keratinic Fibres Containing a Thickening Polymer With an Ether Skeleton.

*Primary Examiner*—Mark Kopec
*Assistant Examiner*—Eisa Elhilo
(74) *Attorney, Agent, or Firm*—Finnegan Henderson Farabow Garrett & Dunner, L.L.P.

(57) ABSTRACT

A ready-to-use composition, a method, and a kit for the bleaching or permanent reshaping of keratin fibers, and in particular human keratin fibers such as the hair, comprising at least one reducing agent and at least one thickening polymer with an aminoplast-ether skeleton. This novel composition, method, and kit can be used to bleach or permanently reshape hair without dripping or falls in viscosity over time.

82 Claims, No Drawings

U.S. PATENT DOCUMENTS

| | | | |
|---|---|---|---|
| 3,966,904 A | 6/1976 | Green et al. ................... 424/78 |
| 4,001,432 A | 1/1977 | Green et al. ................. 424/329 |
| 4,005,193 A | 1/1977 | Green et al. ................. 424/168 |
| 4,025,617 A | 5/1977 | Green et al. ................... 424/78 |
| 4,025,627 A | 5/1977 | Green et al. ............. 424/248.4 |
| 4,025,653 A | 5/1977 | Green et al. ................. 424/325 |
| 4,026,945 A | 5/1977 | Green et al. ................. 260/567 |
| 4,027,008 A | 5/1977 | Sokol ........................... 424/62 |
| 4,027,020 A | 5/1977 | Green et al. ........... 424/248.56 |
| 4,031,307 A | 6/1977 | DeMartino et al. .......... 536/114 |
| 4,157,388 A | 6/1979 | Christiansen ................. 429/70 |
| 4,172,887 A | 10/1979 | Vanlerberghe et al. ........ 424/70 |
| 4,223,009 A | 9/1980 | Chakrabarti ................. 424/47 |
| 4,277,581 A | 7/1981 | Vanlerberghe et al. ...... 525/420 |
| 4,349,532 A | 9/1982 | Vanlerberghe et al. ......... 424/47 |
| 4,390,689 A | 6/1983 | Jacquet et al. ............... 528/335 |
| 4,591,610 A | 5/1986 | Grollier ......................... 524/55 |
| 4,608,250 A | 8/1986 | Jacquet et al. ................. 424/71 |
| 4,702,906 A | 10/1987 | Jacquet et al. ................. 424/70 |
| 4,719,282 A | 1/1988 | Nadolsky et al. ............ 528/310 |
| 4,761,273 A | 8/1988 | Grollier et al. ................ 424/47 |
| 4,839,166 A | 6/1989 | Grollier et al. ................ 424/71 |
| 4,996,059 A | 2/1991 | Grollier et al. ................ 424/71 |
| 5,009,880 A | 4/1991 | Grollier et al. ................ 424/47 |
| 5,139,037 A | 8/1992 | Grollier et al. .............. 132/203 |
| 5,196,189 A | 3/1993 | Jacquet et al. ................. 424/72 |
| 5,914,373 A | 6/1999 | Glancy et al. ............... 525/406 |
| 6,273,920 B1 * | 8/2001 | De La Mettrie et al. ....... 8/401 |

* cited by examiner

COMPOSITION, METHOD, AND KIT FOR THE BLEACHING OR PERMANENT RESHAPING OF KERATIN FIBERS, COMPRISING AT LEAST ONE THICKENING POLYMER WITH AN AMINOPLAST-ETHER SKELETON

The present invention relates to a composition for the bleaching or permanent reshaping of keratin fibers, and in particular of human keratin fibers such as the hair, comprising at least one reducing agent and at least one thickening polymer with an aminoplast-ether skeleton.

It is known practice to bleach keratin fibers, and in particular human hair, with bleaching compositions containing one or more oxidizing agents. Among the oxidizing agents conventionally used, mention may be made of hydrogen peroxide or compounds capable of producing hydrogen peroxide by hydrolysis, such as urea peroxide or persalts, for instance perborates, percarbonates and persulfates, hydrogen peroxide and persulfates being particularly preferred.

However, it is also known practice to bleach human keratin fibers such as the hair, and in particular hair artificially dyed with exogenous colorants, using reducing agents such as ascorbic acid or thiols, for instance cysteine.

It is also known practice to permanently reshape the hair by applying thereto compositions containing one or more reducing agents, the hair preferably having been placed under tension beforehand, in particular with the aid of mechanical devices such as rollers, the hair thus reduced then being reoxidized in the desired shape, usually after rinsing, by means of atmospheric oxygen, but more generally via an oxidizing agent that is preferably chosen from aqueous hydrogen peroxide solution and alkali metal bromates.

The reducing agents preferably used in the context of the permanent reshaping of the hair are thiols such as thioglycolic acid, its salts and its esters, thiolactic acid and its salts, cysteine or cysteamine, and sulfites.

Compositions intended for bleaching the hair using reducing agents are mainly in the form of ready-to-use compositions consisting of anhydrous products (powders or creams) containing the reducing agent(s), which is mixed at the time of use with an aqueous composition optionally containing a pH agent. Bleaching compositions are also in the form of aqueous ready-to-use compositions containing the reducing agent(s) at the appropriate pH.

Reducing compositions for permanently reshaping the hair are generally in the form of ready-to-use aqueous compositions or in the form of pulverulent or liquid anhydrous compositions that are mixed at the time of use with an aqueous composition at the appropriate pH.

To localize the bleaching or permanent reshaping product on application to the hair so that it does not run down the face or beyond the areas which it is proposed to treat, use has been made hitherto of conventional thickeners such as crosslinked polyacrylic acid, hydroxyethylcelluloses, certain polyurethanes, waxes and also, in the case of bleaching compositions, mixtures of nonionic surfactants with an HLB (Hydrophilic-Lipophilic Balance) value, which, when suitably chosen, give rise to the gelling effect when they are diluted with water and/or surfactants.

However, the Applicant-has found that the thickening systems mentioned above do not make it possible to obtain bleaching or permanent reshaping results that are sufficiently intense and homogeneous.

Moreover, the Applicant has also found that ready-to-use compositions for bleaching or permanently reshaping the hair containing the reducing agent(s) and also the thickener systems of the prior art do not allow a sufficiently precise application without running or falls in viscosity over time.

However, after considerable research conducted in this matter, the Applicant has now discovered that it is possible to obtain compositions for bleaching or permanently reshaping the hair, containing at least one reducing agent, that do not run and thus remain satisfactorily localized at the point of application, and that also make it possible to obtain bleaching or permanent reshaping results that are intense and homogeneous, if an effective amount of a polymer with an aminoplast-ether skeleton is introduced into the composition.

These discoveries form the basis of the present invention.

One subject of the present invention is thus a ready-to-use composition for the bleaching or permanent reshaping of keratin fibers, in particular human keratin fibers such as the hair, comprising, in a medium that is suitable for bleaching or permanent reshaping, at least one reducing agent, which is characterized in that it also contains at least one polymer with an aminoplast-ether skeleton.

For the purposes of the invention, the expression "ready-to-use composition" means the composition intended to be applied in unmodified form to the keratin fibers, that is to say that it can be stored in unmodified form before use or can result from the mixing, at the time of use, of two or more compositions.

When the ready-to-use composition according to the invention results from the mixing of several compositions at the time of use, the polymer with an aminoplast-ether skeleton may be present in one or more or in all of the mixed compositions.

Accordingly, the polymer with an aminoplast-ether skeleton may be present in an anhydrous composition in powder form, preferably in pulverulent form or in cream form and/or in one or more aqueous compositions.

Preferably, according to the invention, the polymer(s) with an aminoplast-ether skeleton is(are) present in at least one aqueous composition that is mixed at the time of use with an aqueous or anhydrous composition in powder or cream form and containing at least one reducing agent.

Another preferred form of the invention is a single composition containing the reducing agent(s) and the polymer(s) with an aminoplast-ether skeleton.

Another subject toward which the present invention is directed is an anhydrous composition containing at least one reducing agent and at least one polymer with an aminoplast-ether skeleton, said composition being intended to be diluted before being applied to the fibers.

The invention is also directed toward a bleaching process or a permanent reshaping process for keratin fibers, and in particular for human keratin fibers such as the hair, using the ready-to-use bleaching or permanent reshaping composition as described according to the invention, the application of said composition possibly being followed, in the case of permanent reshaping, by the application, optionally after rinsing, of an oxidizing composition.

The invention is also directed toward bleaching devices or packaging "kits" containing such a ready-to-use composition.

Thus, a two-compartment device comprises a first compartment containing at least one anhydrous powder or cream or an aqueous composition, and the second compartment comprises an aqueous composition, at least one of the two compartments containing at least one reducing agent and at least one of the two compartments containing at least one polymer with an aminoplast-ether skeleton.

However, other characteristics, aspects, subjects and advantages of the invention will emerge even more clearly on reading the description and the examples that follow.

For the purposes of the present invention, the term "aminoplast-ether" means any product derived from the condensation of an aldehyde with an amine or an amide.

For the purposes of the present invention, the term "aminoplast-ether" also means any structural unit formed from an aminoplast residue and a divalent hydrocarbon-based residue linked to the aminoplast residue via an ether bond.

The polymers with an aminoplast-ether skeleton that are used according to the invention are preferably chosen from those containing at least one unit of structure (I) below:

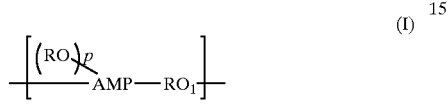

(I)

in which:
AMP is an aminoplast residue with alkylene units,
R denotes a hydrogen atom, a $C_1$–$C_4$ alkyl radical or a $C_1$–$C_4$ acyl radical,
$RO_1$ is a divalent alkyleneoxy residue,
p denotes a positive integer,
the group(s) OR being linked to the alkylene units of the AMP residue.

Preferably, the polymers with an aminoplast-ether skeleton are chosen from those containing at least one unit of structure (II) below:

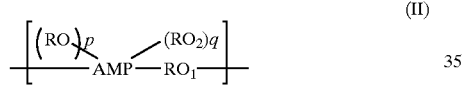

(II)

in which:
AMP, R, $RO_1$ and p have the same meaning as above,
$RO_2$ is a hydrophobic group other than RO linked to AMP via a hetero atom and comprising at least two carbon atoms, and
q is a positive integer.

Even more preferably, the polymers of the invention are of formulae (III) and (IIIa) below:

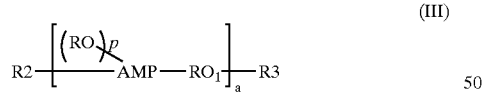

(III)

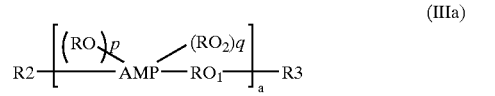

(IIIa)

in which:
AMP, R, $RO_1$, $RO_2$, p and q have the same meaning as above, R2 or R3, which may be identical or different, represent an end group that can denote a hydrogen atom, a group $RO_2H$, a group $RO_2H$, a group AMP(OR)p or any monofunctional group such as alkyl, cycloalkyl, aryl, aralkyl, alkylaryl, alkyloxyalkyl, aryloxyalkyl or cycloalkoxyalkyl,
a being a number greater than 1 and preferably greater than 2.

The aminoplast residues bearing the groups OR thereof integrated into the polymers of the invention may be chosen, in a nonlimiting manner, from structures (IV) to (XV) below:

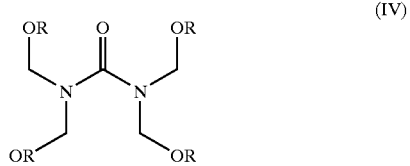

(IV)

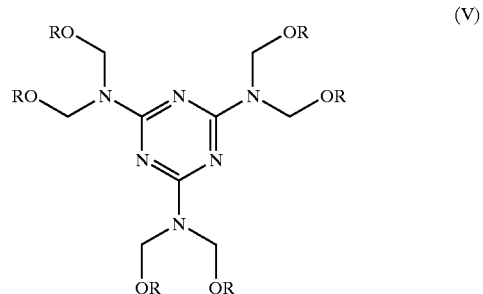

(V)

(VI)

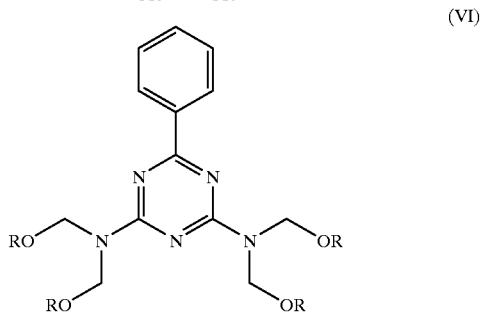

(VII)

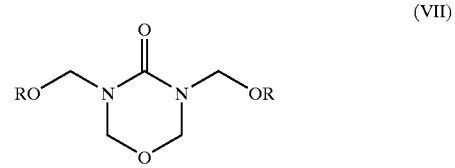

(VIII)

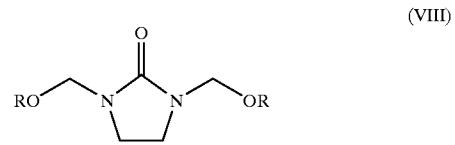

(IX)

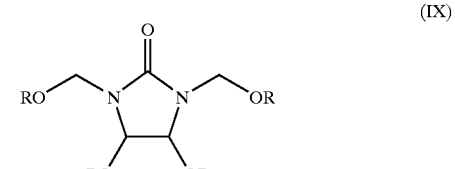

(X)

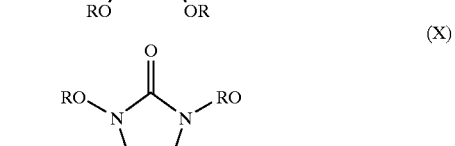

(XI)

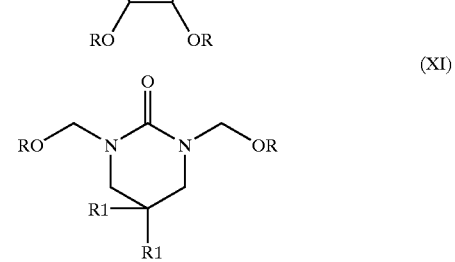

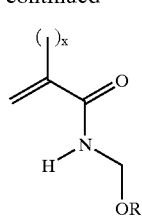

(XII)

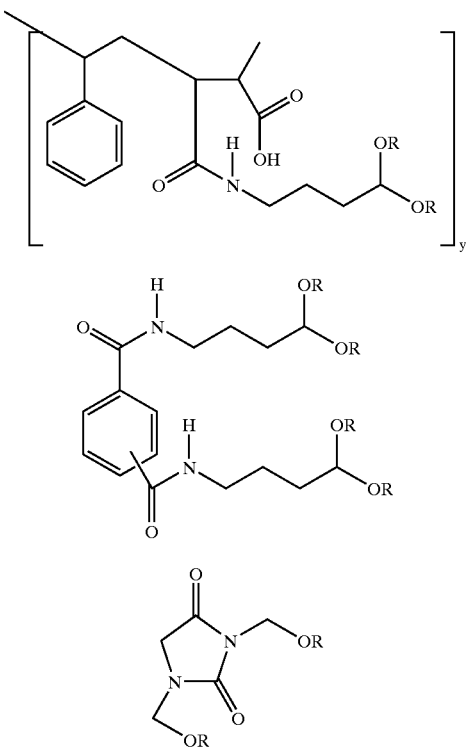

(XIII)

(XIV)

(XV)

in which:
R has the same meaning as above,
R1 denotes $C_1$–$C_4$ alkyl,
y is a number at least equal to 2,
x denotes 0 or 1.

Preferably, the aminoplast residue(s) bearing the groups OR thereof is (are) chosen from those of structure (XVI) below:

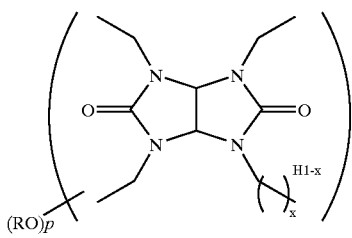

(XVI)

in which R, p and x have the same meanings as above.

The divalent alkyleneoxy residues are preferably those corresponding to the diols of general formula (XVII) below:

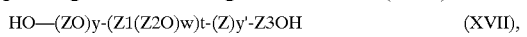 (XVII), y and y' being numbers ranging from 0 to 1000,
t and w being numbers ranging from 0 to 10,
Z, Z', Z2 and Z3 are $C_2$–$C_4$ alkylene radicals and preferably radicals —CH2—CH(Z4)— and —CH2—CH(Z4)—CH2—, Z1 being a linear or cyclic, branched or unbranched, aromatic or nonaromatic radical optionally comprising one or more hetero atoms containing from 1 to 40 carbon atoms,
Z4 denoting a hydrogen atom or a $C_1$–$C_4$ alkyl radical or a $C_1$–$C_3$ acyl radical, it being understood that at least one of the radicals Z4 of the radicals Z, Z', Z2 and Z3 is other than acyl.

Preferably, Z4 denotes a hydrogen atom or a methyl radical.

Even more preferably, t=0 and Z, Z' and Z3 denote —CH2CH2—, and at least one of the groups from among y and y' is other than 0. The compounds of formula (XVII) are then polyethylene glycols.

The aminoplast-ether polymers of formula (I) according to the invention are described in particular in patent U.S. Pat. No. 5,914,373, the content of which forms an integral part of the invention.

As polymers with an aminoplast-ether skeleton of formula (I), mention may be made in particular of the products Pure-Thix L [PEG-180/Octoxynol-40/TMMG Copolymer (INCI name)], Pure-Thix M [PEG-180/Laureth-50/TMMG Copolymer (INCI name)] and Pure-Thix HH [Polyether-1 (INCI name)] sold by the company Sud-Chemie.

The polymers with an aminoplast-ether skeleton are preferably used in an amount that can range from about 0.01% to 10% by weight relative to the total weight of the ready-to-use bleaching or permanent reshaping composition. More preferably, this amount ranges from about 0.1% to 5% by weight.

The reducing agents that may be used according to the invention are preferably chosen from thiols such as cysteine, thioglycolic acid, thiolactic acid, salts thereof and esters thereof, cysteamine and its salts, or sulfites.

In the case of compositions intended for bleaching, it is also possible to use ascorbic acid, its salts and its esters, erythorbic acid, its salts and its esters, and sulfinates, for instance sodium hydroxymethanesulfinate.

These reducing agents are used in said ready-to-use compositions in concentrations of between 0.1% and 30% approximately, and preferably between 0.5°% and 20% approximately, by weight, relative to the total weight of the composition.

More particularly, the compositions according to the invention can also contain at least one cationic or amphoteric substantive polymer.

For the purposes of the present invention, the expression "cationic polymer" denotes any polymer containing cationic groups and/or groups that can be ionized into cationic groups.

The cationic polymers that can be used in accordance with the present invention may be chosen from any of those already known per se as improving the cosmetic properties of the hair, i.e. in particular those described in patent application EP-A-337 354 and in French patents FR-2 270 846, 2 383 660, 2 598 611, 2 470 596 and 2 519 863.

The preferred cationic polymers are chosen from those which contain units containing primary, secondary, tertiary and/or quaternary amine groups which can either form part of the main polymer chain or which can be carried by a lateral substituent that is directly attached thereto.

The cationic polymers used generally have a number-average molecular mass of between 500 and $5 \times 10^6$ approximately, and preferably between $10^3$ and $3 \times 10^6$ approximately.

Among the cationic polymers, mention may be made more particularly of polymers of poly(quaternary ammonium), polyamino amide and polyamine type. These are known products. They are described in particular in French patents Nos. 2 505 348 or 2 542 997. Among said polymers, mention may be made of:
(1) Homopolymers or copolymers derived from acrylic or methacrylic esters or amides and comprising at least one of the units of formula (I), (II), (III) or (IV) below:

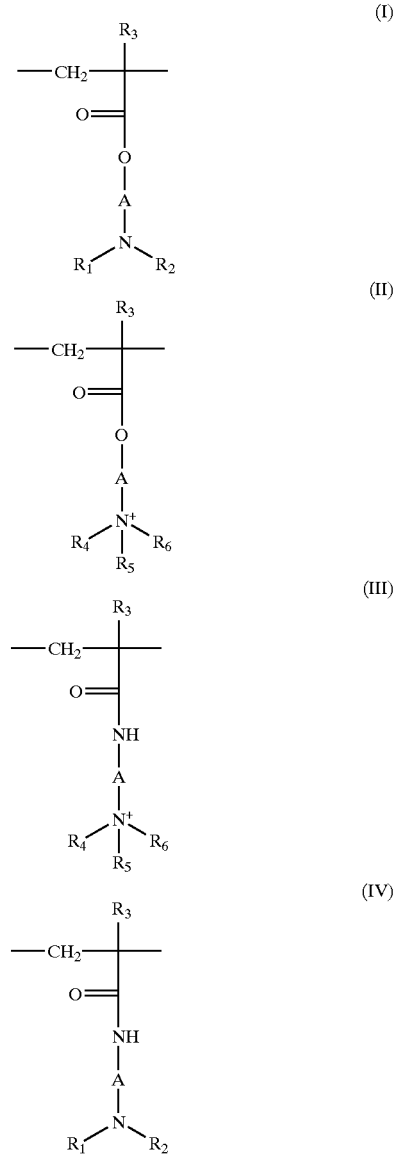

in which:
$R_3$, which may be identical or different, denote a hydrogen atom or a $CH_3$ radical;
A, which may be identical or different, represent a linear or branched alkyl group of 1 to 6 carbon atoms, preferably 2 or 3 carbon atoms, or a hydroxyalkyl group of 1 to 4 carbon atoms;
$R_4$, $R_5$ and $R_6$, which may be identical or different, represent an alkyl group containing from 1 to 18 carbon atoms or a benzyl radical and preferably an alkyl group containing from 1 to 6 carbon atoms;
$R_1$ and $R_2$, which may be identical or different, represent hydrogen or an alkyl group containing from 1 to 6 carbon atoms, and preferably methyl or ethyl; X denotes an anion derived from an inorganic or organic acid, such as a methosulfate anion or a halide such as chloride or bromide.

Polymers of family (1) can also contain one or more units derived from comonomers which may be chosen from the family of acrylamides, methacrylamides, diacetone acrylamides, acrylamides and methacrylamides substituted on the nitrogen with lower —($C_1$–$C_4$) alkyls, acrylic or methacrylic acids or esters thereof, vinyllactams such as vinylpyrrolidone or vinylcaprolactam, and vinyl esters.

Thus, among these polymers of family (1), mention may be made of:
copolymers of acrylamide and of dimethylaminoethyl methacrylate quaternized with dimethyl sulfate or with a dimethyl halide, such as the product sold under the name Hercofloc by the company Hercules,
the copolymers of acrylamide and of methacryloyloxy-ethyltrimethylammonium chloride described, for example, in patent application EP-A-080 976 and sold under the name Bina Quat P 100 by the company Ciba Geigy,
the copolymer of acrylamide and of methacryloyloxy-ethyltrimethylammonium methosulfate sold under the name Reten by the company Hercules,
quaternized or non-quaternized vinylpyrrolidone/dialkylaminoalkyl acrylate or methacrylate copolymers, such as the products sold under the name "Gafquat" by the company ISP, such as, for example, "Gafquat 734" or "Gafquat 755", or alternatively the products known as "Copolymer 845, 958 and 937". These polymers are described in detail in French patents 2 077 143 and 2 393 573,
dimethylaminoethyl methacrylate/vinylcaprolactam/vinylpyrrolidone terpolymers, such as the product sold under the name Gaffix VC 713 by the company ISP,
vinylpyrrolidone/methacrylamidopropyldimethylamine copolymers sold in particular under the name Styleze CC 10 by ISP, and
quaternized vinylpyrrolidone/dimethylaminopropyl-methacrylamide copolymers such as the product sold under the name "Gafquat HS 100" by the company ISP.
(2) The cellulose ether derivatives containing quaternary ammonium groups, described in French patent 1 492 597, and in particular polymers sold under the names "JR" (JR 400, JR 125 and JR 30M) or "LR" (LR 400, or LR 30M) by the company Union Carbide Corporation. These polymers are also defined in the CTFA dictionary as quaternary ammoniums of hydroxyethylcellulose that has reacted with an epoxide substituted with a trimethylammonium group.
(3) Cationic cellulose derivatives such as cellulose copolymers or cellulose derivatives grafted with a water-soluble monomer of quaternary ammonium, and described in particular in U.S. Pat. No. 4,131,576, such as hydroxyalkylcelluloses, for instance hydroxymethyl-, hydroxyethyl- or hydroxypropylcelluloses grafted, in particular, with a methacryloylethyltrimethylammonium, methacrylamidopropyltrimethylammonium or dimethyldiallylammonium salt.
The commercial products corresponding to this definition are more particularly the products sold under the names "Celquat L 200" and "Celquat H 100" by the company National Starch.
(4) The cationic polysaccharides described more particularly in U.S. Pat. Nos. 3,589,578 and 4,031,307, such as guar gums containing cationic trialkylammonium groups. Guar gums modified with a salt (e.g. chloride) of 2,3-epoxypropyltrimethylammonium are used, for example.
Such products are sold in particular under the trade names Jaguar C13 S, Jaguar C 15, Jaguar C 17 or Jaguar C162 by the company Meyhall.

(5) Polymers consisting of piperazinyl units and of divalent alkylene or hydroxyalkylene radicals containing straight or branched chains, optionally interrupted by oxygen, sulfur or nitrogen atoms or by aromatic or heterocyclic rings, as well as the oxidation and/or quaternization products of these polymers. Such polymers are described, in particular, in French patents 2 162 025 and 2 280 361.

(6) Water-soluble polyamino amides prepared in particular by polycondensation of an acidic compound with a polyamine; these polyamino amides can be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or alternatively with an oligomer resulting from the reaction of a difunctional compound which is reactive with a bis-halohydrin, a bis-azetidinium, a bis-haloacyldiamine, a bis-alkyl halide, an epihalohydrin, a diepoxide or a bis-unsaturated derivative; the crosslinking agent is used in proportions ranging from 0.025 to 0.35 mol per amine group of the polyamino amide; these polyamino amides can be alkylated or, if they contain one or more tertiary amine functions, they can be quaternized. Such polymers are described, in particular, in French patents 2 252 840 and 2 368 508.

(7) The polyamino amide derivatives resulting from the condensation of polyalkylene polyamines with polycarboxylic acids followed by alkylation with difunctional agents. Mention may be made, for example, of adipic acid/dialkylaminohydroxyalkyldialkylene-triamine polymers in which the alkyl radical contains from 1 to 4 carbon atoms and preferably denotes methyl, ethyl or propyl. Such polymers are described in particular in French patent 1 583 363.

Among these derivatives, mention may be made more particularly of the adipic acid/dimethylamino-hydroxypropyl/diethylenetriamine polymers sold under the name "Cartaretine F, F4 or F8" by the company Sandoz.

(8) The polymers obtained by reaction of a polyalkylene polyamine containing two primary amine groups and at least one secondary amine group with a dicarboxylic acid chosen from diglycolic acid and saturated aliphatic dicarboxylic acids having from 3 to 8 carbon atoms. The molar ratio between the polyalkylene polyamine and the dicarboxylic acid is between 0.8:1 and 1.4:1; the polyamino amide resulting therefrom is reacted with epichlorohydrin in a molar ratio of epichlorohydrin relative to the secondary amine group of the polyamino amide of between 0.5:1 and 1.8:1. Such polymers are described in particular in U.S. Pat. Nos. 3,227,615 and 2,961,347.

Polymers of this type are sold in particular under the name "Hercosett 57" by the company Hercules Inc. or alternatively under the name "PD 170" or "Delsette 101" by the company Hercules in the case of the adipic acid/epoxypropyl/diethylenetriamine copolymer.

(9) Cyclopolymers of alkyldiallylamine or of dialkyldiallylammonium, such as the homopolymers or copolymers containing, as main constituent of the chain, units corresponding to formula (V) or (VI):

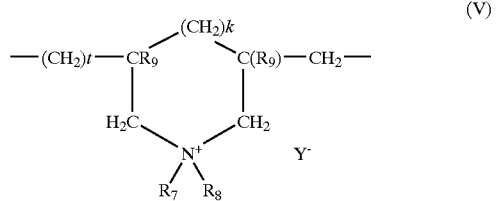

(V)

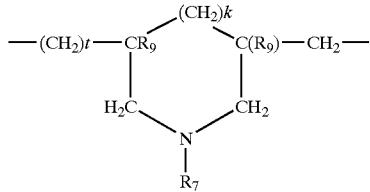

(VI)

in which formulae k and t are equal to 0 or 1, the sum k+t being equal to 1; $R_9$ denotes a hydrogen atom or a methyl radical; $R_7$ and $R_8$, independently of each other, denote an alkyl group having from 1 to 22 carbon atoms, a hydroxyalkyl group in which the alkyl group preferably has 1 to 5 carbon atoms, a lower $C_1$–$C_4$ amidoalkyl group, or $R_7$ and $R_8$ can denote, together with the nitrogen atom to which they are attached, heterocyclic groups such as piperidyl or morpholinyl; $R_7$ and $R_8$, independently of each other, preferably denote an alkyl group containing from 1 to 4 carbon atoms; Y is an anion such as bromide, chloride, acetate, borate, citrate, tartrate, bisulfate, bisulfite, sulfate or phosphate. These polymers are described in particular in French patent 2 080 759 and in its Certificate of Addition 2 190 406.

Among the polymers defined above, mention may be made more particularly of the dimethyldiallylammonium chloride homopolymer sold under the name "Merquat 100" by the company Calgon (and its homologues of low weight-average molecular mass) and copolymers of diallyldimethylammonium chloride and of acrylamide, sold under the name "Merquat 550".

(10) The quaternary diammonium polymer containing repeating units corresponding to the formula:

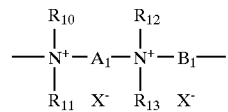

(VII)

in which formula (VII):

$R_{10}$, $R_{11}$, $R_{12}$ and $R_{13}$, which may be identical or different, represent aliphatic, alicyclic or arylaliphatic radicals containing from 1 to 20 carbon atoms or lower hydroxyalkylaliphatic radicals, or alternatively $R_{10}$, $R_{11}$, $R_{12}$ and $R_{13}$, together or separately, constitute, with the nitrogen atoms to which they are attached, heterocycles optionally containing a second hetero atom other than nitrogen, or alternatively $R_{10}$, $R_{11}$, $R_{12}$ and $R_{13}$ represent a linear or branched $C_1$–$C_6$ alkyl radical substituted with a nitrile, ester, acyl or amide group pr a group —CO-O—$R_{14}$—D or —CO—NH—$R_{14}$—D where $R_{14}$ is an alkylene and D is a quaternary ammonium group;

$A_1$ and $B_1$ represent polymethylene groups containing from 2 to 20 carbon atoms which may be linear or branched, saturated or unsaturated, and which may contain, linked to or intercalated in the main chain, one or more aromatic rings or one or more oxygen or sulfur atoms or sulfoxide, sulfone, disulfide, amino, alkylamino, hydroxyl, quaternary ammonium, ureido, amide or ester groups, and X denotes an anion derived from an inorganic or organic acid;

$A_1$, $R_{10}$ and $R_{12}$ can form, with the two nitrogen atoms to which they are attached, a piperazine ring; in addition, if $A_1$ denotes a linear or branched, saturated or unsaturated alkylene or hydroxyalkylene radical, $B_1$ can also denote a group —(CH$_2$)$_n$—CO—D—OC—CH$_2$)$_n$— in which D denotes:
a) a glycol residue of formula: —O—Z—O—, where Z denotes a linear or branched hydrocarbon radical or a group corresponding to one of the following formulae:

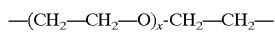

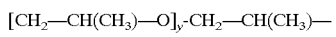

where x and y denote an integer from 1 to 4, representing a defined and unique degree of polymerization or any number from 1 to 4 representing an average degree of polymerization;
b) a bis-secondary diamine residue such as a piperazine derivative;
c) a bis-primary diamine residue of formula: —NH—Y—NH—, where Y denotes a linear or branched hydrocarbon radical, or alternatively the divalent radical

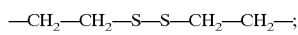

d) a ureylene group of formula: —NH—CO—NH—.
Preferably, X$^-$ is an anion such as chloride or bromide.
These polymers generally have a number-average molecular mass of between 1000 and 100,000.
Polymers of this type are described in particular in French patents 2 320 330, 2 270 846, 2 316 271, 2 336 434 and 2 413 907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.
It is more particularly possible to use polymers that consist of repeating units corresponding to the formula (VIII) below:

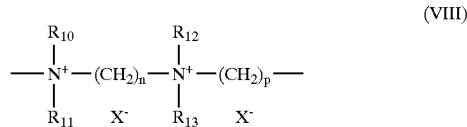

in which R$_{10}$, R$_{11}$, R$_{12}$ and R$_{13}$, which may be identical or different, denote an alkyl or hydroxyalkyl radical containing from 1 to 4 carbon atoms approximately, n and p are integers ranging from 2 to 20 approximately, and X$^-$ is an anion derived from a mineral or organic acid.
(11) Poly(quaternary ammonium) polymers consisting of units of formula (IX):

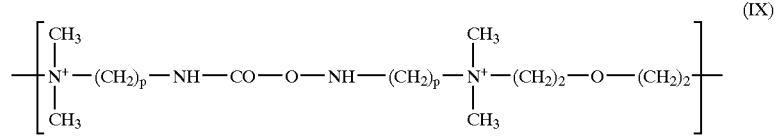

in which:
p denotes an integer ranging from 1 to 6 approximately,
D can be zero or can represent a group —(CH$_2$)$_r$—CO— in which r denotes a number equal to 4 or 7, and
X$^-$ is an anion derived from a mineral or organic acid.
The cationic polymers comprising units of formula (IX) are disclosed in particular in patent application EP-A-122 324 and may be prepared according to the processes disclosed in U.S. Pat. Nos. 4,157,388, 4,390,689, 4,702,906 and 4,719,282.
Among these polymers, the ones that are preferred are those with a molecular mass, measured by carbon-13 NMR, of less than 100 000, and in the formula of which:
p is equal to 3, and
a) D represents a group —(CH$_2$)$_4$—CO—, X denotes a chlorine atom, the molecular mass, measured by carbon-13 NMR (C$^{13}$ NMR), being about 5600; a polymer of this type is proposed by the company Miranol under the name Mirapol-AD1,
b) D represents a group —(CH$_2$)$_2$—CO— and X denotes a chlorine atom, the molecular mass, measured by carbon-13 NMR (C$^{13}$ NMR), being about 8100; a polymer of this type is proposed by the company Miranol under the name Mirapol-AZ1,
c) D denotes the value zero and X denotes a chlorine atom, the molecular mass, measured by carbon-13 NMR (C$^{13}$ NMR), being about 25 500; a polymer of this type is sold by the company Miranol under the name Mirapol-A15,
d) a "block copolymer" formed from units corresponding to the polymers described in paragraphs a) and c), sold by the company Miranol under the names Mirapol-9 (C$^{13}$ NMR molecular mass of about 7800), Mirapol-175 (C$^{13}$ NMR molecular mass of about 8000) and Mirapol-95 (C$^{13}$ NMR molecular mass of about 12 500).
Even more particularly, the polymer which is preferred according to the invention is a polymer containing units of formula (IX) in which p is equal to 3, D denotes the value zero and X denotes a chlorine atom, the molecular mass, measured by carbon-13 NMR (C$^{13}$ NMR), being about 25 500.
(12) Quaternary polymers of vinylpyrrolidone and of vinylimidazole, such as, for example, the products sold under the names Luviquat FC 905, FC 550 and FC 370 by the company BASF.
(13) Polyamines such as Polyquart H sold by Henkel under the reference name "Polyethylene glycol (15) tallow polyamine" in the CTFA dictionary.
(14) Crosslinked methacryloyloxy(C$_1$–C$_4$)alkyltri-(C$_1$–C$_4$) alkylammonium salt polymers such as the polymers obtained by homopolymerization of dimethylaminoethylmethacrylate quaternized with methyl chloride, or by copolymerization of acrylamide with dimethylaminoethyl methacrylate quaternized with methyl chloride, the homo- or copolymerization being followed by crosslinking with a compound containing olefinic unsaturation, in particular methylenebisacrylamide. A crosslinked acrylamide/methacryloyloxyethyltrimethyl-ammonium chloride copolymer (20/80 by weight) in the form of a dispersion containing 50% by weight of said copolymer in mineral oil can be used more particularly. This dispersion is sold under the name "Salcare® SC 92" by the company Allied Colloids. A crosslinked methacryloyloxyethyltrimethylammonium chloride homopolymer containing about 50% by weight of the homopolymer in mineral oil or in a liquid ester can also be used. These dispersions are sold under the names "Salcare® SC 95" and "Salcare® SC 96" by the company Allied Colloids.

Other cationic polymers which can be used in the context of the invention are polyalkyleneimines, in particular polyethyleneimines, polymers containing vinylpyridine or vinylpyridinium units, condensates of polyamines and of epichlorohydrin, quaternary polyureylenes and chitin derivatives.

Among all the cationic polymers which can be used in the context of the present invention, it is preferred to use the polymers of families (1), (9), (10), (11) and (14) and even more preferably the polymers of formulae (W) and (U) below:

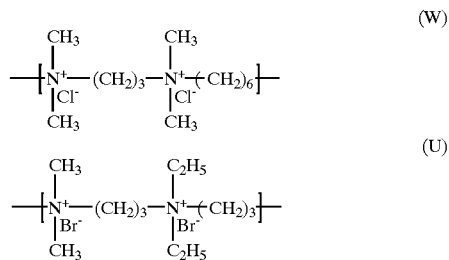

and in particular those in which the molecular weight, determined by gel permeation chromatography, is between 9500 and 9900;
and in particular those in which the molecular weight, determined by gel permeation chromatography, is about 1200.

The concentration of cationic polymers in the compositions according to the present invention can range from 0.01% to 10% by weight relative to the total weight of the composition, preferably from 0.05% to 5% and even more preferably from 0.1% to 3%.

The amphoteric polymers which can be used in accordance with the present invention can be chosen from polymers containing units K and M distributed randomly in the polymer chain, in which K denotes a unit derived from a monomer containing at least one basic nitrogen atom and M denotes a unit derived from an acid monomer containing one or more carboxylic or sulfonic groups, or alternatively K and M can denote groups derived from carboxybetaine or sulfobetaine zwitterionic monomers;
K and M can also denote a cationic polymer chain containing primary, secondary, tertiary or quaternary amine groups, in which at least one of the amine groups bears a carboxylic or sulfonic group connected via a hydrocarbon radical or alternatively K and M form part of a chain of a polymer containing an α,β-dicarboxylic ethylene unit in which one of the carboxylic groups has been made to react with a polyamine containing one or more primary or secondary amine groups.

The amphoteric polymers corresponding to the definition given above which are more particularly preferred are chosen from the following polymers:

(1) Polymers resulting from the copolymerization of a monomer derived from a vinyl compound bearing a carboxylic group such as, more particularly, acrylic acid, methacrylic acid, maleic acid, α-chloroacrylic acid, and a basic monomer derived from a substituted vinyl compound containing at least one basic atom, such as, more particularly, dialkylaminoalkyl methacrylates and acrylates, dialkylaminoalkylmethacrylamides and -acrylamides. Such compounds are described in U.S. Pat. No. 3,836,537. Mention may also be made of the sodium acrylate/acrylamidopropyltrimethylammonium chloride copolymer sold under the name Polyquart KE 3033 by the company Henkel.

The vinyl compound can also be a dialkyldiallylammonium salt such as dimethyldiallylammonium chloride. The copolymers of acrylic acid and of the latter monomer are sold under the names Merquat 280, Merquat 295 and Merquat Plus 3330 by the company Calgon.

(2) Polymers containing units derived from:
a) at least one monomer chosen from acrylamides and methacrylamides substituted on the nitrogen with an alkyl radical,
b) at least one acidic comonomer containing one or more reactive carboxylic groups, and
c) at least one basic comonomer such as esters containing primary, secondary, tertiary and quaternary amine substituents of acrylic and methacrylic acids and the product of quaternization of dimethylaminoethyl methacrylate with dimethyl or diethyl sulfate.

The N-substituted acrylamides or methacrylamides which are more particularly preferred according to the invention are groups in which the lkyl radicals contain from 2 to 12 carbon atoms and more particularly N-ethylacrylamide, N-tert-butylacryl-amide, N-tert-octylacrylacide, N-octylacrylamide, N-decylacrylamide, N-dodecylacrylamide and the corresponding methacrylamides.

The acidic comonomers are chosen more particularly from acrylic acid, methacrylic acid, crotonic acid, itaconic acid, maleic acid and fumaric acid and alkyl monoesters, having 1 to 4 carbon atoms, of maleic or fumaric acids or anhydrides.

The preferred basic comonomers are aminoethyl, butylaminoethyl, N,N'-dimethylaminoethyl and N-tert-butylaminoethyl methacrylates.

The copolymers whose CTFA (4th edition, 1991) name is octylacrylamide/acrylates/butylaminoethyl methacrylate copolymer such as the products sold under the name Amphomer or Lovocryl 47 by the company National Starch are particularly used.

(3) Crosslinked and alkylated polyamino amides partially or totally derived from polyamino amides of general formula:

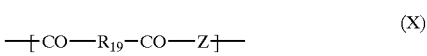

in which $R_{19}$ represents a divalent radical derived from a saturated dicarboxylic acid, a mono- or dicarboxylic aliphatic acid containing an ethylenic double bond, an ester of a lower alkanol, having 1 to 6 carbon atoms, of there acids or a radical derived from the addition of any one of said acids to a bis(primary) or bis(secondary) amine, and Z denotes a bis(primary), mono- or bis(secondary) polyalkylene-polyamine radical and preferably represents:

a) in proportions of from 60 to 100 mol %, the radical

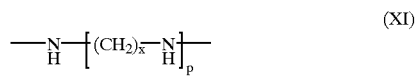

where x=2 and p=2 or 3, or alternatively x=3 and p=2 this radical being derived from die hylene mine, from triethylenetetraamine or from dipropylenetriamine;

b) in proportions of from 0 to 40 mol %, the radical (XI) above in which x=2 and p=1 and which is derived from ethylenediamine, or the radical derived from piperazine:

c) in proportions of from 0 to 20 mol %, the —NH—(CH$_2$)$_6$—NH— radical derived from hexamethylenediamine, these polyamino amines being crosslinked by addition of a difunctional crosslinking agent chosen from epihalohydrins, diepoxides, dianhydrides and bis-unsaturated derivatives, using from 0.025 to 0.35 mol of crosslinking agent per amine group of the polyamino amide and alkylated by the action of acrylic acid, chloroacetic acid or an alkane sulfone, or salts thereof.

The saturated carboxylic acids are preferably chosen from acids having 6 to 10 carbon atoms, such as adipic acid, 2,2,4-trimethyladipic acid and 2,4,4-trimethyladipic acid, terephthalic acid, acids containing an ethylenic double bond such as, for example, acrylic acid, methacrylic acid and itaconic acid.

The alkane sultones used in the alkylation are preferably propane sultone or butane sultone, the salts of the alkylating agents are preferably the sodium or potassium salts.

(4) Polymers containing zwitterionic units of formula:

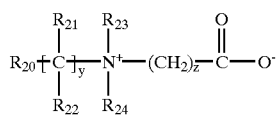

(XII)

in which R$_{20}$ denotes a polymerizable unsaturated group such as an acrylate, methacrylate, acrylamide or methacrylamide group, y and z represent an integer from 1 to 3, R$_{21}$ and R$_{22}$ represent a hydrogen atom, methyl, ethyl or propyl, R$_{23}$ and R$_{24}$ represent a hydrogen atom or an alkyl radical such that the sum of the carbon atoms in R$_{23}$ and R$_{24}$ does not exceed 10.

The polymers comprising such units can also contain units derived from non-zwitterionic monomers such as dimethyl or diethylaminoethyl acrylate or methacrylate or alkyl acrylates or methacrylates, acrylamides or methacrylamides or vinyl acetate.

By way of example, mention may be made of the copolymer of methyl methacrylate/dimethyl-carboxymethylammonio ethyl methacrylate such as the product sold under the name Diaformer Z301 by the company Sandoz.

(5) Polymers derived from chitosan containing monomer units corresponding to the following formulae (XIII), (XIV), (XV):

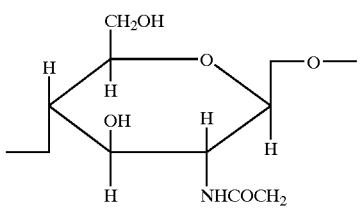

(XIII)

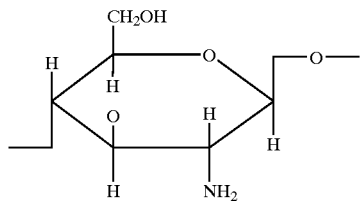

(XIV)

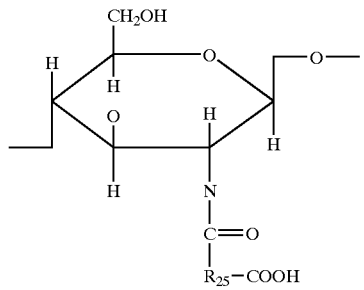

(XV)

the unit (XIII) being present in proportions of between 0 and 30%, the unit (XIV) in proportions of between 5 and 50% and the unit F in proportions of between 30 and 90%, it being understood that, in this unit (XV), R$_{25}$ represents a radical of formula:

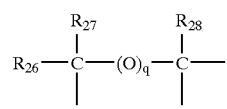

in which if q=0, R$_{26}$, R$_{27}$ and R$_{28}$, which may be identical or different, each represent a hydrogen atom, a methyl, hydroxyl, acetoxy or amino residue, a monoalkylamine residue or a dialkylamine residue which are optionally interrupted by one or more nitrogen atoms and/or optionally substituted with one or more amine, hydroxyl, carboxyl, alkylthio or sulfonic groups, an alkylthio residue in which the alkyl group bears an amino residue, at least one of the radicals R$_{26}$, R$_{27}$ and R$_{28}$ being, in this case, a hydrogen atom;

or, if q=1, R$_{26}$, R$_{27}$ and R$_{28}$ each represent a hydrogen atom, as well as the salts formed by these compounds with bases or acids.

(6) Polymers derived from the N-carboxyalkylation of chitosan, such as N-carboxymethylchitosan or N-carboxybutylchitosan sold under the name "Evalsan" by the company Jan Dekker.

(7) Polymers corresponding to the general formula (XI) such as those described, for example, in French patent 1 400 366:

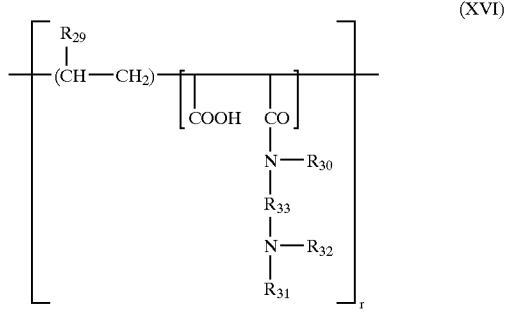

(XVI)

in which $R_{29}$ represents a hydrogen atom, a $CH_3O$, $CH_3CH_2O$ or phenyl radical, $R_{30}$ denotes hydrogen or a lower alkyl radical such as methyl or ethyl, $R_{31}$ denotes hydrogen or a lower alkyl radical such as methyl or ethyl, $R_{32}$ denotes a lower alkyl radical such as methyl or ethyl or a radical corresponding to the formula: $-R_{33}-N(R_{31})_2$, $R_{33}$ representing a $-CH_2-CH_2-$, $-CH_2-CH_2-CH_2-$ or $-CH_2-CH(CH_3)-$ group, $R_{31}$ having the meanings mentioned above,
as well as the higher homologues of these radicals and containing up to 6 carbon atoms.

(8) Amphoteric polymers of the type $-D-X-D-X-$ chosen from:

a) polymers obtained by the action of chloroacetic acid or sodium chloroacetate on compounds containing at least one unit of formula:

where D denotes a radical

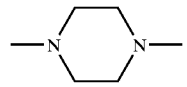

and X denotes the symbol E or E', E or E', which may be identical or different, denoting a divalent radical which is an alkylene radical containing a straight or branched chain containing up to 7 carbon atoms in the main chain, which is unsubstituted or substituted with hydroxyl groups and which can contain, in addition to the oxygen, nitrogen and sulfur atoms, 1 to 3 aromatic and/or heterocyclic rings; the oxygen, nitrogen and sulfur atoms being present in the form of ether, thioether, sulfoxide, sulfone, sulfonium, alkylamine or alkenylamine groups, hydroxyl, benzylamine, amine oxide, quaternary ammonium, amide, imide, alcohol, ester and/or urethane groups;

b) Polymers of formula:

in which D denotes a radical

and X denotes the symbol E or E' and at least once E'; E having the meaning given above and E' is a divalent radical which is an alkylene radical with a straight or ranched chain having up to 7 carbon atoms in the main chain, which is unsubstituted or substituted with one or more hydroxyl radicals and containing one or more nitrogen atoms, the nitrogen atom being substituted with an alkyl chain which is optionally interrupted by an oxygen atom and necessarily containing one or more carboxyl functions or one or more hydroxyl functions and betainized by reaction with chloroacetic acid or sodium chloroacetate.

(9) $(C_1-C_5)$alkyl vinyl ether/maleic anhydride copolymers partially modified by semiamidation with an N,N-dialkylaminoalkylamine such as N,N-dimethylaminopropylamine or by semiesterification with an N,N-dialkanolamine. These copolymers can also contain other vinyl comonomers such as vinylcaprolactam.

The amphoteric polymers that are particularly preferred according to the invention are those of family (1).

According to the invention, the amphoteric polymer(s) can represent from 0.01% to 10% by weight, preferably from 0.05% to 5% by weight and even more preferably from 0.1% to 3% by weight, relative to the total weight of the composition.

The compositions of the invention preferably comprise one or more surfactants.

The surfactant(s) can be chosen without preference, alone or as mixtures, from anionic, amphoteric, nonionic, zwitterionic and cationic surfactants.

The surfactants that are suitable for carrying out the present invention are, in particular, the following:

(i) Anionic Surfactant(s):

As examples of anionic surfactants which can be used, alone or as mixtures, in the context of the present invention, mention may be made in particular (nonlimiting list) of salts (in particular alkaline salts, especially sodium salts, ammonium salts, amine salts, amino alcohol salts or magnesium salts) of the following compounds: alkyl sulfates, alkyl ether sulfates, alkylamido ether sulfates, alkylarylpolyether sulfates, monoglyceride sulfates; alkyl sulfonates, alkyl phosphates, alkylamide sulfonates, alkylaryl sulfonates, α-olefin sulfonates, paraffin sulfonates; $(C_6-C_{24})$ alkyl sulfosuccinates, $(C_6-C_{24})$ alkyl ether sulfosuccinates, $(C_6-C_{24})$ alkylamide sulfosuccinates; $(C_6-C_{24})$ alkyl sulfoacetates; $(C_6-C_{24})$ acyl sarcosinates and $(C_6-C_{24})$ acyl glutamates. It is also possible to use the carboxylic esters of $(C_6-C_{24})$ alkylpolyglycosides, such as alkylglucoside citrates, alkypolyglycoside tartrates and alkylpolyglycoside sulfosuccinates, alkylsulfosuccinamates; acyl isethionates and N-acyltaurates, the alkyl or acyl radical of all of these various compounds preferably containing from 12 to 20 carbon atoms, and the aryl radical preferably denoting a phenyl or benzyl group. Among the anionic surfactants which can also be used, mention may also be made of fatty acid salts such as the salts of oleic, ricinoleic, palmitic and stearic acids, coconut oil acid or hydrogenated coconut oil acid; acyl lactylates in which the acyl radical contains 8 to 20 carbon atoms. Alkyl-D-galactosideuronic acids and their salts, polyoxyalkylenated $(C_6-C_{24})$ alkyl ether carboxylic acids, polyoxyalkylenated $(C_6-C_{24})$ alkylaryl ether carboxylic acids, polyoxyalkylenated $(C_6-C_{24})$ alkylamido ether carboxylic acids and their salts, in particular those containing from 2 to 50 alkylene oxide, in particular ethylene oxide, groups, and mixtures thereof can also be used.

(ii) Nonionic Surfactant(s):

The nonionic surfactants are also compounds that are well known per se (see in particular in this respect "Handbook of Surfactants" by M. R. Porter, published by Blackie & Son (Glasgow and London), 1991, pp. 116–178) and, in the context of the present invention, their nature is not a critical feature. Thus, they can be chosen in particular from (nonlimiting list) polyethoxylated or polypropoxylated alkylphenols, α-diols or alcohols having a fatty chain containing, for example, 8 to 18 carbon atoms, it being possible for the number of ethylene oxide or propylene oxide groups to range in particular from 2 to 50. Mention may also be made of copolymers of ethylene oxide and of propylene oxide, condensates of ethylene oxide and of propylene oxide with fatty alcohols; polyethoxylated fatty amides preferably having from 2 to 30 mol of ethylene oxide, polyglycerolated fatty amides containing on average 1 to 5, and in particular 1.5 to 4, glycerol groups; oxyethylenated fatty acid esters of sorbitan having from 2 to 30 mol of ethylene oxide; fatty acid esters of sucrose, fatty acid esters of polyethylene glycol, alkylpolyglycosides, N-alkylglucamine derivatives, amine oxides such as ($C_{10}$–$C_{14}$)alkylamine oxides or N-acylaminopropylmorpholine oxides.

(iii) Amphoteric or Zwitterionic Surfactant(s):

The amphoteric or zwitterionic surfactants, whose nature is not a critical feature in the context of the present invention, can be, in particular (non-limiting list), aliphatic secondary or tertiary amine derivatives in which the aliphatic radical is a linear or branched chain containing 8 to 18 carbon atoms and containing at least one water-soluble anionic group (for example carboxylate, sulfonate, sulfate, phosphate or phosphonate); mention may also be made of ($C_8$–$C_{20}$)alkylbetaines, sulfobetaines, ($C_8$–$C_{20}$)alkylamido ($C_1$–$C_6$)alkylbetaines or ($C_8$–$C_{20}$)alkylamido($C_1$–$C_6$) alkylsulfobetaines.

Among the amine derivatives, mention may be made of the products sold under the name Miranol, as described in U.S. Pat. Nos. 2,528,378 and 2,781,354 and classified in the CTFA dictionary, 3rd edition, 1982, under the names amphocarboxyglycinates and amphocarboxypropionates of respective structures:

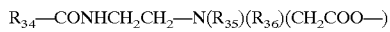

$R_{34}$—CONHCH$_2$CH$_2$—N($R_{35}$)($R_{36}$)(CH$_2$COO—)

in which: $R_{34}$ denotes an alkyl radical derived from an acid $R_{34}$—COOH present in hydrolyzed coconut oil, a heptyl, nonyl or undecyl radical, $R_{35}$ denotes a β-hydroxyethyl group and $R_{36}$ denotes a carboxymethyl group; and

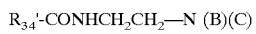

$R_{34}$'-CONHCH$_2$CH$_2$—N (B)(C)

in which:
B represents —CH$_2$CH$_2$OX', C represents —(CH$_2$)—Y', with z=1 or 2,
X' denotes the —CH$_2$CH$_2$—COOH group or a hydrogen atom,
Y' denotes —COOH or the —CH$_2$—CHOH—SO$_3$H radical,
$R_{34}$' denotes an alkyl radical of an acid $R_{37}$—COOH present in coconut oil or in hydrolyzed linseed oil, an alkyl radical, in particular a $C_7$, $C_9$, $C_{11}$, or $C_{13}$ alkyl radical, a $C_{17}$ alkyl radical and its iso form, an unsaturated $C_{17}$ radical.

These compounds are classified in the CTFA dictionary, 5th edition, 1993, under the names disodium cocoamphodiacetate, disodium lauroamphodiacetate, disodium caprylamphodiacetate, disodium caprylamphodiacetate, disodium cocoamphodipropionate, disodium lauroamphodipropionate, disodium caprylamphodipropionate, disodium caprylamphodipropionate, lauroamphodipropionic acid and cocoamphodipropionic acid.

By way of example, mention may be made of the cocoamphodiacetate sold under the trade name Miranol® C2M Concentrate by the company Rhodia Chimie.

(iv) Cationic Surfactants:

Among the cationic surfactants which may be mentioned in particular (nonlimiting list) are: primary, secondary or tertiary fatty amine salts, optionally polyoxyalkylenated; quaternary ammonium salts such as tetraalkylammonium, alkylamidoalkyltrialkylammonium, trialkylbenzylammonium, trialkylhydroxyalkylammonium or alkylpyridinium chlorides or bromides; imidazoline derivatives; or amine oxides of cationic nature.

The amounts of surfactants present in the ready-to-use composition according to the invention can range from 0.01% to 30% and preferably from 0.1% to 20% relative to the total weight of the composition.

The compositions according to the invention can also contain other agents for adjusting the rheology, such as cellulosic thickeners (hydroxyethylcellulose, hydroxypropylcellulose, carboxymethylcellulose, etc.), guar gum and its derivatives (hydroxypropyl guar, etc.), gums of microbial origin (xanthan gum, scleroglucan gum, etc.), synthetic thickeners such as crosslinked acrylic acid or acrylamidopropanesulfonic acid homopolymers and ionic or nonionic associative polymers such as the polymers sold under the names Pemulen TR1 or TR2 by the company Goodrich, Salcare SC90 by the company Allied Colloids, Aculyn 22, 28, 33, 44 or 46 by the company Rohm & Haas, and Elfacos T210 and T212 by the company Akzo.

These additional thickeners can represent from 0.05% to 10% by weight relative to the total weight of the composition.

The pH of the ready-to-use composition is generally between about 1.5 and 12.

More preferably, the pH of the ready-to-use compositions of the invention that are intended for bleaching is between about 1.5 and 10, and even more preferably between about 1.5 and 7.

More preferably, the pH of the ready-to-use compositions of the invention that are intended for permanent reshaping is between about 6 and 12, and even more preferably between about 7 and 11.

This pH may be adjusted to the desired value by means of acidifying or basifying agents that are well known in the prior art in the bleaching or permanent reshaping of keratin fibers.

Among the basifying agents that may be mentioned, for example, are aqueous ammonia, alkali metal carbonates or ammonium carbonate, alkanolamines such as monoethanolamine, diethanolamine and triethanolamine and also derivatives thereof, oxyethylenated and/or oxypropylenated hydroxyalkylamines and ethylenediamines, sodium hydroxide, potassium hydroxide and the compounds of formula (XIX) below:

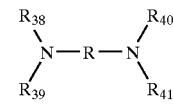

(XIX)

in which R is a propylene residue optionally substituted with a hydroxyl group or a $C_1$–$C_4$ alkyl radical; $R_{38}$, $R_{39}$, $R_{40}$ and $R_{41}$, which may be identical or different, represent a hydrogen atom, a $C_1$–$C_4$ alkyl radical or a $C_1$–$C_4$ hydroxyalkyl radical.

The acidifying agents are conventionally, for example, mineral or organic acids, for instance hydrochloric acid, orthophosphoric acid, carboxylic acids, for instance tartaric acid, citric acid or lactic acid, or sulfonic acids.

The basifying or acidifying agents can represent about 0.01% to 30% by weight relative to the total weight of the bleaching or permanent reshaping composition.

The compositions of the invention can also contain sequestering agents such as, for example, ethylenediaminetetraacetic acid (EDTA).

When the compositions containing the reducing agent and the polymer with an aminoplast-ether skeleton are in anhydrous form (powder or cream), they contain the main agents and additives mentioned above in the form of essentially anhydrous solids or liquids. They can also contain mineral or organic fillers such as silicas or clays. They can also contain binders such as vinylpyrrolidone, oils or waxes, polyalkylene glycols or polyalkylene glycol derivatives. They can also contain lubricants, for instance polyol stearates or alkali metal or alkaline-earth metal stearates, and also colorants or matt-effect agents, for instance titanium oxides.

When the medium containing the reducing agent is an aqueous medium, it can optional ly contain cosmetically acceptable organic solvents more particularly including alcohols such as ethyl alcohol, isopropyl alcohol, benzyl alcohol and phenylethyl alcohol, or glycols or glycol ethers such as, for example, ethylene glycol monomethyl, monoethyl or monobutyl ether, propylene glycol or its ethers such as, for example, propylene glycol monomethyl ether, butylene glycol, dipropylene glycol and also diethylene glycol alkyl ethers such as, for example, diethylene glycol monoethyl ether or monobutyl ether, in concentrations of between about 0.5% and 20, an preferably between about 2% and 10%, by weight relative to the total weight of the composition.

The bleaching or permanent reshaping composition according to the invention may also contain an effective amount of other agents, which are previously known elsewhere for the bleaching or permanent reshaping of keratin fibers, such as various common-adjuvants, for instance volatile or nonvolatile, cyclic or linear or branched silicones, which are organomodified (especially with amine groups) or not organomodified, preserving agents, ceramides, plant, mineral or synthetic waxes or oils, acids and in particular AHAs, etc.

Needless to say, a person skilled in the art will take care to select the optional additional compound(s) mentioned above, such that the advantageous properties intrinsically associated with the composition for bleaching or permanently reshaping keratin fibers according to the invention are not, or are not substantially, adversely affected by the envisaged addition(s).

The bleaching process according to the invention preferably consists in applying the ready-to-use reducing composition to wet or dry keratin fibers, and leaving the composition to act for an exposure time preferably ranging from 1 to 60 minutes approximately, and more preferably from 10 to 45 minutes approximately, rinsing the fibers and then optionally washing them with shampoo, followed by rinsing them again and drying them.

Preferably, the permanent reshaping process according to the invention consists in applying the ready-to-use reducing composition to wet or dry keratin fibers, leaving it to act for an exposure time preferably ranging from 1 to 60 minutes approximately and more preferably from 10 to 45 minutes approximately, optionally rinsing the fibers and then applying an oxidizing composition and leaving it to act for an exposure time of between 1 and 20 minutes and preferably between 1 and 10 minutes, and then optionally washing the fibers with shampoo, followed by rinsing them again and drying them.

Mechanical means for placing the keratin fibers under tension may be used before, during or after applying the reducing composition, and removed before or after rinsing out the oxidizing composition.

Concrete examples illustrating the invention are given below, without, however, having any limiting nature.

EXAMPLE 1

The ready-to-use aqueous bleaching composition below was prepared (expressed in grams):

| | |
|---|---|
| Citric acid | 7.4 |
| Trisodium citrate dihydrate | 1 |
| Hydroxyethylcellulose | 1.5 |
| 2-Oxoglutaric acid | 0.8 |
| Sodium ascorbate | 57 |
| L-Cysteine | 2 |
| Pure-Thix-HH (INCI = Polyether-1) | 0.3 AM* |
| Magnesium sulfate | 1 |
| Water            qs | 100 |

AM* = Active Material

The above bleaching composition gave a uniform bleaching of hair artificially dyed with an oxidizing dye.

EXAMPLE 2

The permanent reshaping composition below was prepared (expressed in grams):

| | |
|---|---|
| Thioglycolic acid | 9.2 |
| Aqueous ammonia containing 20% NH$_3$ | 9.3 |
| Ammonium carbonate | 4.5 |
| Cocoylamidopropylbetaine/glyceryl monolaurate (25/5) | 0.4 AM* |
| EDTA | 0.4 |
| Cationic polymer of formula W as a 60% solution in water | 1 AM* |
| Pure-Thix-HH (INCI = Polyether-1) | 0.3 AM* |
| Water            qs | 100 |

AM* = Active Material

The above permanent reshaping composition was applied for 15 minutes to wet hair rolled up beforehand on hairsetting rollers, and then rinsed out thoroughly with water. An 8-volumes aqueous hydrogen peroxide solution of pH 3 was then applied for 5 minutes, the hair was then rinsed again, the rollers were removed and the hair was dried.

The hair had beautiful uniform curls.

What is claimed is:

1. A ready-to-use composition for the bleaching or permanent reshaping of keratin fibers comprising, in a medium suitable for bleaching or permanent reshaping, at least one reducing agent, and at least one thickening polymer with an aminoplast-ether skeleton.

2. The composition according to claim 1, wherein said at least one thickening polymer with an aminoplast-ether skeleton corresponds to the general structure (I):

$$\left[ \underset{\left[(RO)_p\right]}{AMP - RO_1} \right] \quad (I)$$

wherein:
  AMP is an aminoplast residue with alkylene units;
  R is chosen from a hydrogen atom, a $C_1$–$C_4$ alkyl radical, and a $C_1$–$C_4$ acyl radical;
  $RO_1$ is a divalent alkyleneoxy residue;

p is a positive integer; and

RO is a hydrophobic group linked to the alkylene units of the AMP residue.

3. The composition according to claim 1, wherein said at least one thickening polymer with an aminoplast-ether skeleton corresponds to the general structure (II):

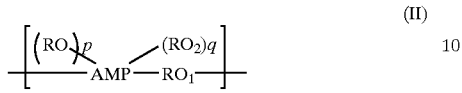
(II)

wherein:

AMP is an aminoplast residue with alkylene units;

R is chosen from a hydrogen atom, a $C_1$–$C_4$ alkyl radical, and a $C_1$–$C_4$ acyl radical;

$RO_1$ is a divalent alkyleneoxy residue;

RO is a hydrophobic group linked to the alkylene units of the AMP residue;

$RO_2$ is a hydrophobic group other than RO linked to the AMP residue via a hetero atom and comprising at least two carbon atoms; and p and q are positive integers.

4. The composition according to claim 1, wherein said at least one thickening polymer with an aminoplast-ether skeleton is chosen from structures (III) and (IIIa):

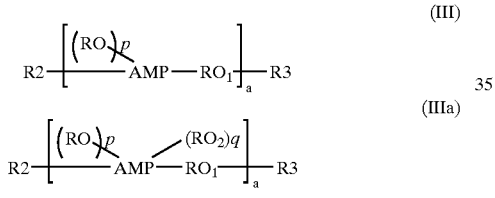
(III)

(IIIa)

wherein:

AMP is an aminoplast residue with alkylene units;

R is chosen from a hydrogen atom, a $C_1$–$C_4$ alkyl radical, and a $C_1$–$C_4$ acyl radical;

$RO_1$ is a divalent alkyleneoxy residue;

RO is a hydrophobic group linked to the alkylene units of the AMP residue;

$RO_2$ is a hydrophobic group other than RO linked to the AMP residue via a hetero atom and comprising at least two carbon atoms;

p and q are positive integers;

R2 and R3, which may be identical or different, represent an end group chosen from a hydrogen atom, a $RO_1H$ group, a $RO_2H$ group, a AMP(OR)p group, and a monofunctional group; and a is a number greater than 1.

5. The composition according to claim 4, wherein said monofunctional group is chosen from an alkyl, a cycloalkyl, an aryl, an aralkyl, an alkylaryl, an alkyloxyalkyl, an aryloxyalkyl, and a cycloalkoxyalkyl.

6. The composition according to claim 2, wherein said aminoplast residue is chosen from structures (IV), (V), (VI), (VII), (VIII), (IX), (X), (XI), (XII), (XIII), (XIV), and (XV):

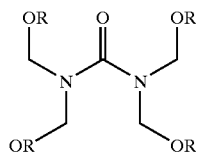
(IV)

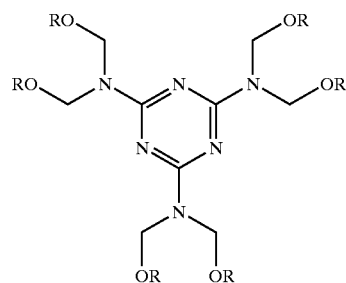
(V)

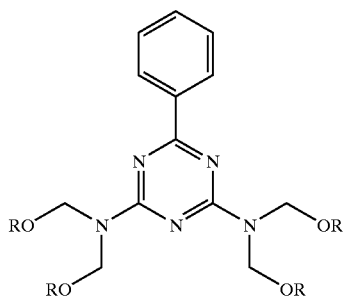
(VI)

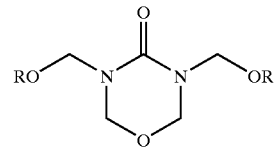
(VII)

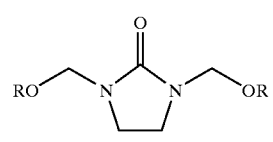
(VIII)

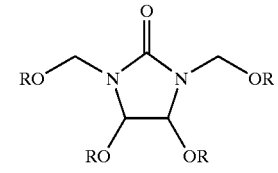
(IX)

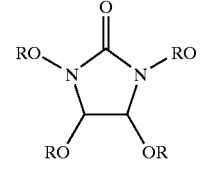
(X)

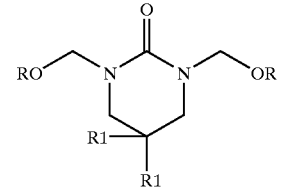
(XI)

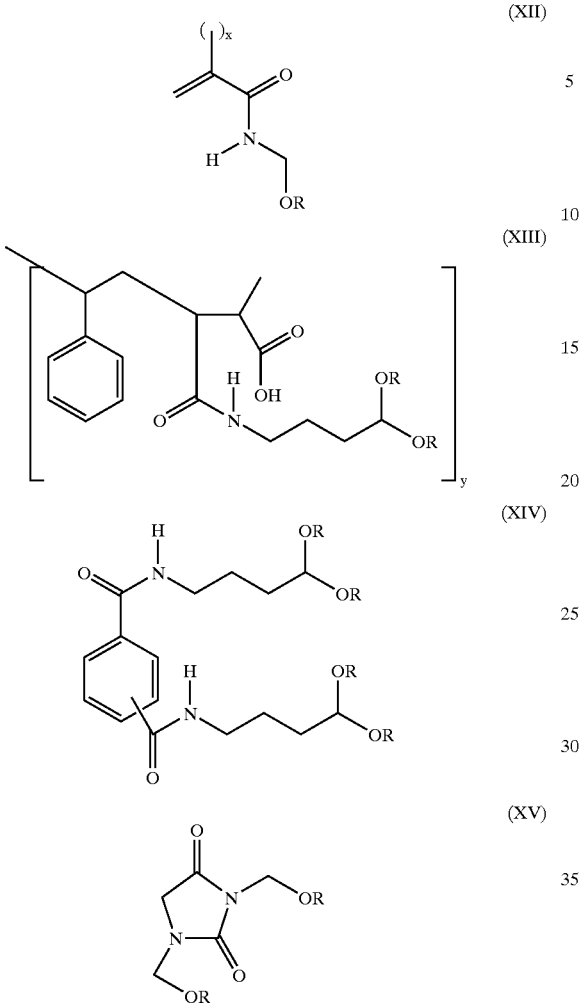
wherein:
R is chosen from a hydrogen atom, a $C_1$–$C_4$ alkyl radical, and a $C_1$–$C_4$ acyl radical;
R1 is a $C_1$–$C_4$ alkyl;
y is a number at least equal to 2; and
x is 0 or 1.
7. The composition according to claim 3, wherein said aminoplast residue is chosen from structures (IV), (V), (VI), (VII), (VIII), (IX), (X), (XI), (XII), (XIII), (XIV), and (XV):
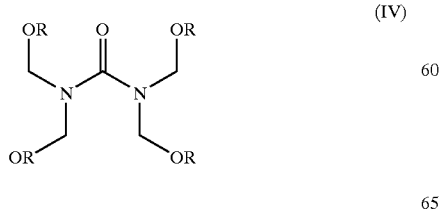
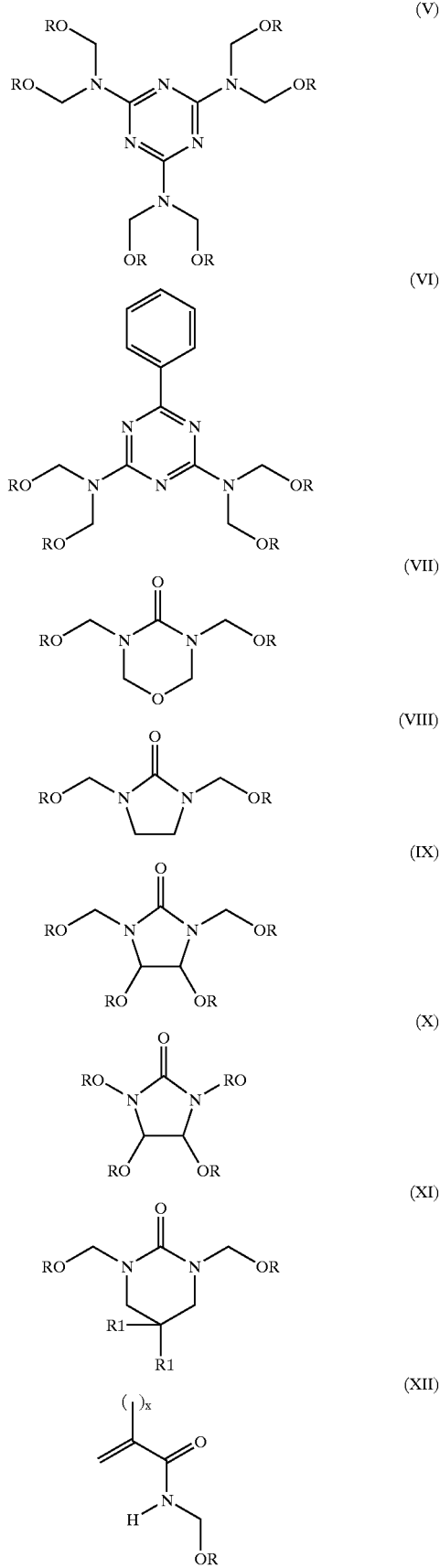

(XIII)
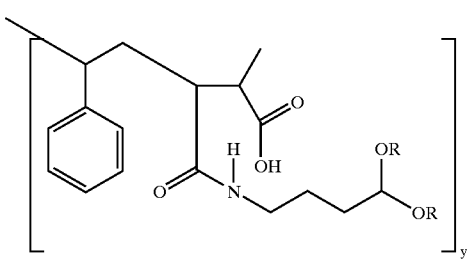
(XIV)
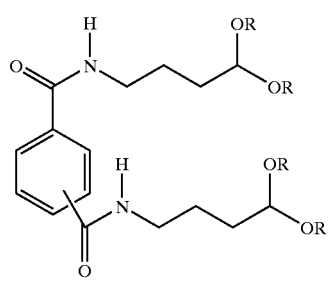
(XV)
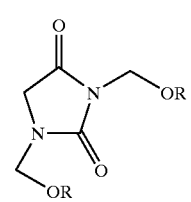
wherein:
R is chosen from a hydrogen atom, a $C_1$–$C_4$ alkyl radical, and a $C_1$–$C_4$ acyl radical;
R1 is a $C_1$–$C_4$ alkyl;
y is a number at least equal to 2; and
x is 0 or 1.
8. The composition according to claim 4, wherein said aminoplast residue is chosen from structures (IV), (V), (VI), (VII), (VIII), (IX), (X), (XI), (XII), (XIII), (XIV), and (XV):
(IV)
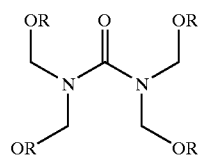
(V)
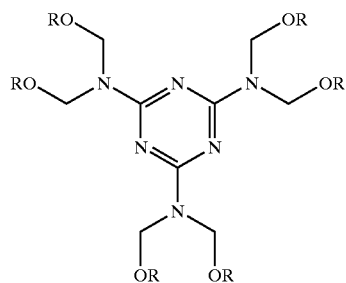
(VI)
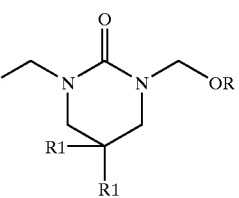
(VII)
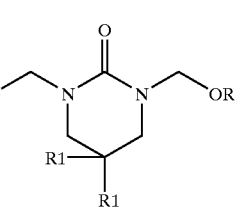
(VIII)
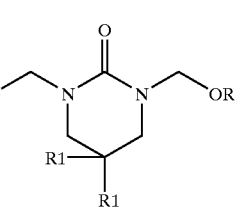
(IX)
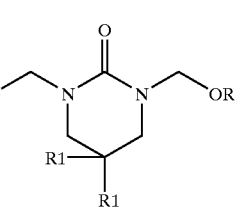
(X)
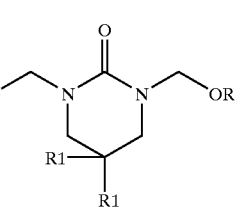
(XI)
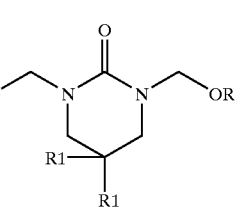
(XII)
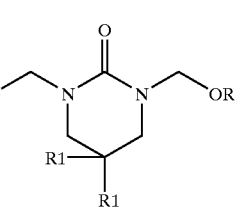
(XIII)
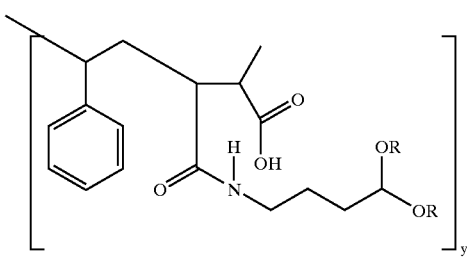

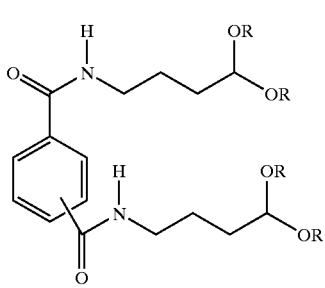

(XIV)

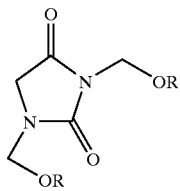

(XV)

wherein:

R is chosen from a hydrogen atom, a $C_1$–$C_4$ alkyl radical, and a $C_1$–$C_4$ acyl radical;

R1 is a $C_1$–$C_4$ alkyl;

y is a number at least equal to 2; and x is 0 or 1.

9. The composition according to claim 2, wherein said aminoplast residue corresponds to structure (XVI):

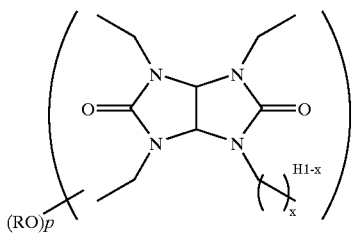

(XVI)

wherein:

R is chosen from a hydrogen atom, a $C_1$–$C_4$ alkyl radical, and a $C_1$–$C_4$ acyl radical;

p is a positive integer; and is 0 or 1.

10. The composition according to claim 3, wherein said aminoplast residue corresponds to structure (XVI):

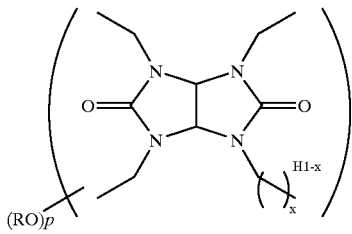

(XVI)

wherein:

R is chosen from a hydrogen atom, a $C_1$–$C_4$ alkyl radical, and a $C_1$–$C_4$ acyl radical;

p is a positive integer; and x is 0 or 1.

11. The composition according to claim 4, wherein said aminoplast residue corresponds to structure (XVI):

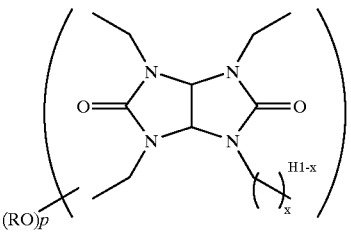

(XVI)

wherein:

R is chosen from a hydrogen atom, a $C_1$–$C_4$ alkyl radical, and a $C_1$–$C_4$ acyl radical;

p is a positive integer; and x is 0 or 1.

12. The composition according to claim 2, wherein said alkyleneoxy residue corresponds to a diol of the general formula (XVII):

$$HO—(ZO)y-(Z1(Z2O)w)t-(Z'O)y'-Z3OH \quad (XVII)$$

wherein:

y and y' are numbers ranging from 0 to 1000;

t and w are numbers ranging from 0 to 10;

Z, Z', Z2 and Z3 are $C_2$–$C_4$ alkylene radicals; and

Z1 is chosen from a linear or cyclic, branched or unbranched, aromatic or nonaromatic radical optionally comprising one or more hetero atoms containing from 1 to 40 carbon atoms.

13. The composition according to claim 3, wherein said alkyleneoxy residue corresponds to a diol of the general formula (XVII):

$$HO—(ZO)y-(Z1\ (Z2O)w)t-(Z'O)y'-Z3OH \quad (XVII)$$

wherein:

y and y' are numbers ranging from 0 to 1000;

t and w are numbers ranging from 0 to 10;

Z, Z', Z2 and Z3 are $C_2$–$C_4$ alkylene radicals; and

Z1 is chosen from a linear or cyclic, branched or unbranched, aromatic or nonaromatic radical optionally comprising one or more hetero atoms containing from 1 to 40 carbon atoms.

14. The composition according to claim 4, wherein said alkyleneoxy residue corresponds to a diol of the general formula (XVII):

$$HO—(ZO)y-(Z1\ (Z2O)w)t-(Z'O)y'-Z3OH \quad (XVII)$$

wherein:

y and y' are numbers ranging from 0 to 1000;

t and w are numbers ranging from 0 to 10;

Z, Z', Z2 and Z3 are $C_2$–$C_4$ alkylene radicals; and

Z1 is chosen from a linear or cyclic, branched or unbranched, aromatic or nonaromatic radical optionally comprising one or more hetero atoms containing from 1 to 40 carbon atoms.

15. The composition according to claim 12, wherein Z, Z', Z2 and Z3 are chosen from radicals —CH2—CH(Z4)— and —CH2—CH(Z4)—CH2—, wherein Z4 is chosen from a hydrogen atom, a $C_1$–$C_4$ alkyl radical, and a $C_1$–$C_3$ acyl radical, with the proviso that at least one of the radicals Z4 is other than acyl.

16. The composition according to claim 12, wherein Z, Z', Z2 and Z3 are chosen from radicals —CH2—CH(Z4)— and —CH2—CH(Z4)—CH2—, wherein Z4 is chosen from a hydrogen atom and a methyl radical.

17. The composition according to claim 13, wherein Z, Z', Z2 and Z3 are chosen from radicals —CH2—CH(Z4)— and —CH2—CH(Z4)—CH2—, wherein Z4 is chosen from a hydrogen atom, a $C_1$–$C_4$ alkyl radical, and a $C_1$–$C_3$ acyl radical, with the proviso that at least one of the radicals Z4 is other than acyl.

18. The composition according to claims 13, wherein Z, Z', Z2 and Z3 are chosen from radicals —CH2—CH(Z4)— and —CH2—CH(Z4)—CH2—, wherein Z4 is chosen from a hydrogen atom and a methyl radical.

19. The composition according to claim 14, wherein Z, Z', Z2 and Z3 are chosen from radicals —CH2—CH(Z4)— and —CH2—CH(Z4)—CH2—, wherein Z4 is chosen from a hydrogen atom, a $C_1$–$C_4$ alkyl radical, and a $C_1$–$C_3$ acyl radical, with the proviso that at least one of the radicals Z4 is other than acyl.

20. The composition according to claim 14, wherein Z, Z', Z2 and Z3 are chosen from radicals —CH2—CH(Z4>and —CH2—CH(Z4)—CH2—, wherein Z4 is chosen from a hydrogen atom and a methyl radical.

21. The composition according to claim 12, wherein t=0; and Z, Z' and Z3 denote —CH2CH2—, wherein at least one from among y and y' has a value other than 0.

22. The composition according to claim 13, wherein t=0; and Z, Z' and Z3 denote —CH2CH2—, wherein at least one from among y and y' has a value other than 0.

23. The composition according to claim 14, wherein t=0; and Z, Z' and Z3 denote —CH2CH2—, wherein at least one from among y and y' has a value other than 0.

24. The composition according to claim 1, wherein said at least one thickening polymer with an aminoplast-ether skeleton is chosen from PEG-180/Octoxynol-40/TMMG Copolymer, PEG-180/Laureth-50/TMMG Copolymer, and Polyether-1.

25. The composition according to claim 1, wherein said at least one thickening polymer with an aminoplast-ether skeleton is present in an amount ranging from 0.01% to 10% by weight relative to the total weight of the composition.

26. The composition according to claim 25, wherein said at least one thickening polymer with an aminoplast-ether skeleton is present in an amount ranging from 0.1% to 5% by weight relative to the total weight of the composition.

27. The composition according to claim 1, wherein said at least one reducing agent is chosen from thiols, cysteamine and its salts, and sulfites.

28. The composition according to claim 27, wherein the thiols are chosen from cysteine, thioglycolic acid, thiolactic acid, salts thereof, and esters thereof.

29. The composition according to claim 1, wherein said at least one reducing agent is chosen from ascorbic acid, its salts and its esters, and erythorbic acid, its salts and its esters.

30. The composition according to claim 27, wherein said at least one reducing agent is present in an amount ranging from 0.1% to 30% by weight relative to the total weight of the composition.

31. The composition according to claim 30, wherein said at least one reducing agent is present in an amount ranging from 0.5% to 20% by weight relative to the total weight of the composition.

32. The composition according to claim 1, further comprising at least one cationic or amphoteric polymer.

33. The composition according to claim 32, wherein said at least one cationic polymer is a poly(quaternary ammonium) polymer having repeat units corresponding to formula (W):

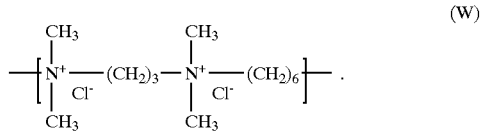

(W)

34. The composition according to claim 32, wherein said at least one cationic polymer is a poly(quaternary ammonium) polymer having repeat units corresponding to formula (U):

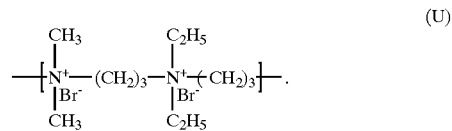

(U)

35. The composition according to claim 32, wherein said at least one amphoteric polymer is a copolymer comprising at least, as monomers, acrylic acid and a dimethyldiallylammonium salt.

36. The composition according to claim 32, wherein said at least one cationic or amphoteric polymer is present in an amount ranging from 0.01% to 10% by weight relative to the total weight of the composition.

37. The composition according to claim 36, wherein said at least one cationic or amphoteric polymer is present in an amount ranging from 0.05% to 5% by weight relative to the total weight of the composition.

38. The composition according to claim 37, wherein said at least one cationic or amphoteric polymer is present in an amount ranging from 0.1% to 3% by weight relative to the total weight of the composition.

39. The composition according to claim 1, further comprising at least one surfactant chosen from anionic, cationic, nonionic and amphoteric surfactants.

40. The composition according to claim 39, wherein said at least one surfactant is present in an amount ranging from 0.01% to 30% by weight relative to the total weight of the composition.

41. The composition according to claim 40, wherein said at least one surfactant is present in an amount ranging from 0.1% to 20% by weight relative to the total weight of the composition.

42. The composition according to claim 1, further comprising at least one additional thickener.

43. The composition according to claim 42, wherein said at least one additional thickener is chosen from a cellulose derivative, a guar derivative, a gum of microbial origin, and a synthetic thickener.

44. The composition according to claim 42, wherein said at least one additional thickener is present in an amount ranging from 0.05% to 10% by weight relative to the total weight of the composition.

45. The composition according to claim 1, further comprising at least one acidifying or basifying agent in an amount ranging from 0.01% to 30% by weight relative to the total weight of the composition.

46. The composition according to claim 45, wherein said at least one basifying agent is chosen from aqueous ammonia, alkali metal carbonates, alkanolamines, oxyethylenated and/or oxypropylenated hydroxyalkylamines and ethylenediamines, sodium hydroxide, potassium hydroxide and the compounds of formula (XIX) below:

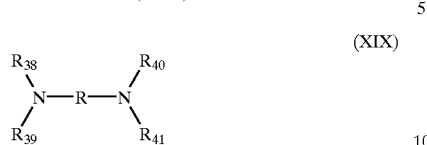

(XIX)

wherein:

R is a propylene residue optionally substituted with a hydroxyl group or a $C_1$–$C_4$ alkyl radical; and $R_{38}$, $R_{39}$, $R_{40}$ and $R_{41}$, which may be identical or different, are chosen from a hydrogen atom, a $C_1$–$C_4$ alkyl radical, and a $C_1$–$C_4$ hydroxyalkyl radical.

47. The composition according to claim 46, wherein said alkanolamine is chosen from at least one of monoethanolamine, diethanolamine, triethanolamine, and derivatives thereof.

48. The composition according to claim 45, wherein said at least one acidifying agent is chosen from mineral acids and organic acids.

49. The composition according to claim 48, wherein said mineral acids and organic acids are chosen form hydrochloric acid, orthophosphoric acid, carboxylic acids, and sulfonic acids.

50. The composition according to claim 49, wherein said carboxylic acids are chosen from tartaric acid, citric acid and lactic acid.

51. The composition according to claim 1, obtained by extemporaneously mixing, at the time of use, at least one anhydrous composition containing at least one reducing agent and at least one aqueous composition, wherein at least one of the anhydrous and aqueous compositions contains at least one thickening polymer with an aminoplast-ether skeleton.

52. An anhydrous composition for the bleaching or permanent reshaping keratin fibers, comprising:

(a) at least one reducing agent, and (b) at least one thickening polymer with an aminoplast-ether skeleton.

53. The composition according to claim 52, wherein said at least one thickening polymer with an aminoplast-ether skeleton corresponds to the general structure (I):

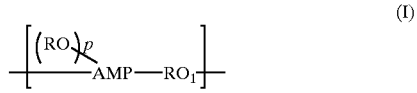

(I)

wherein:

AMP is an aminoplast residue with alkylene units;

R is chosen from a hydrogen atom, a $C_1$–$C_4$ alkyl radical, and a $C_1$–$C_4$ acyl radical;

$RO_1$ is a divalent alkyleneoxy residue;

p is a positive integer; and

RO is a hydrophobic group linked to the alkylene units of the AMP residue.

54. The composition according to claim 52, wherein said at least one thickening polymer with an aminoplast-ether skeleton corresponds to the general structure (II):

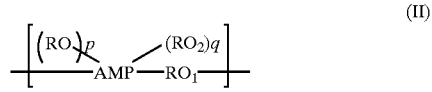

(II)

wherein:

AMP is an aminoplast residue with alkylene units;

R is chosen from a hydrogen atom, a $C_1$–$C_4$ alkyl radical, and a $C_1$–$C_4$ acyl radical;

$RO_1$ is a divalent alkyleneoxy residue;

RO is a hydrophobic group linked to the alkylene units of the AMP residue;

$RO_2$ is a hydrophobic group other than RO linked to the AMP residue via a hetero atom and comprising at least two carbon atoms; and p and q are positive integers.

55. The composition according to claim 52, wherein said at least one thickening polymer with an aminoplast-ether skeleton is chosen from structures (III) and (IIIa):

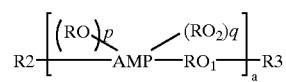

(III)

(IIIa)

wherein:

AMP is an aminoplast residue with alkylene units;

R is chosen from a hydrogen atom, a $C_1$–$C_4$ alkyl radical, and a $C_1$–$C_4$ acyl radical;

$RO_1$ is a divalent alkyleneoxy residue;

RO is a hydrophobic group linked to the alkylene units of the AMP residue;

$RO_2$ is a hydrophobic group other than RO linked to the AMP residue via a hetero atom and comprising at least two carbon atoms;

p and q are positive integers;

R2 and R3, which may be identical or different, represent an end group chosen from a hydrogen atom, a $RO_1H$ group, a $RO_2H$ group, a AMP(OR)p group and a monofunctional group; and a is a number greater than 1.

56. The composition according to claim 51, wherein said at least one anhydrous composition is in pulverulent form.

57. The composition according to claim 52, wherein said at least one anhydrous composition is in pulverulent form.

58. The composition according to claim 51, wherein said at least one anhydrous composition contains at least one additive chosen from mineral and organic fillers, binders, lubricants, and colorants or matt-effect agents.

59. The composition according to claim 58, wherein said mineral and organic fillers are silica or clays, said binders are vinylpyrrolidone, oils or waxes, polyalkylene glycols or polyalkylene glycol derivatives, said lubricants are polyol stearates or alkali metal or alkaline-earth metal stearates, and said colorants or matt-effect agents are titanium oxides.

60. The composition according to claim 58, wherein each of said at least one additive is present in an amount ranging from 0% to 30% by weight relative to the total weight of the composition.

61. The composition according to claim 1, wherein said composition is aqueous.

62. The composition according to claim 61, wherein said composition contains at least one organic solvent.

63. The composition according to claim 62, wherein said at least one organic solvent is present in an amount ranging from 0.5% to 20% by weight relative to the total weight of the composition.

64. The composition according to claim 63, wherein said at least one organic solvent is present in an amount ranging from 2% to 10% by weight relative to the total weight of the composition.

65. The composition according to claim 1, having a pH ranging from 1.5 to 12.

66. The composition according to claim 1, for the bleaching of keratin fibers, having a pH ranging from 1.5 to 10.

67. The composition according to claim 66, wherein the pH ranges from 1.5 to 7.

68. The composition according to claim 1, for the permanent reshaping of keratin fibers, having a pH ranging from 6 to 12.

69. The composition according to claim 68, wherein the pH ranges from 7 to 11.

70. The composition according to claim 51, wherein said thickening polymer with an aminoplast-ether skeleton is in said at least one aqueous composition.

71. A method for bleaching or permanently reshaping keratin fibers, said method comprising:

(a) applying a ready-to-use composition to wet or dry keratin fibers, in a medium suitable for bleaching or permanent reshaping, wherein said medium contains at least one reducing agent, and at least one thickening polymer with an aminoplast-ether skeleton, and (b) rinsing the fibers after leaving said composition in contact with said keratin fibers for a period of time ranging from 1 to 60 minutes.

72. The method according to claim 71, wherein said composition is left in contact with said keratin fibers for a period of time ranging from 10 to 45 minutes.

73. The method according to claim 71, further comprising washing the keratin fibers with shampoo and rinsing the keratin fibers.

74. The method according to claim 73, further comprising drying the keratin fibers.

75. The method according to claim 71, further comprising, following the rinsing step, the application of an oxidizing composition to the keratin fibers and the rinsing of the fibers after leaving said oxidizing composition in contact with said fibers for a period of time ranging from 1 to 20 minutes.

76. The method according to claim 75, wherein said oxidizing composition is left in contact with said keratin fibers for a period of time ranging from 1 to 10 minutes.

77. The method according to claim 75, further comprising washing the keratin fibers with shampoo and rinsing the keratin fibers.

78. The method according to claim 77, further comprising drying the keratin fibers.

79. A two-compartment device or kit for the bleaching or permanent reshaping of keratin fibers, wherein the first compartment contains at least one pulverant or at least one aqueous composition, and the second compartment contains at least one aqueous composition, wherein at least one of the two compartments contains at least one reducing agent and at least one of the two compartments contains at least one thickening polymer with an aminoplast-ether skeleton.

80. The device or kit according to claim 79, wherein said at least one thickening polymer with an aminoplast-ether skeleton corresponds to the general structure (I):

(I)

wherein:

AMP is an aminoplast residue with alkylene units;

R is chosen from a hydrogen atom, a $C_1$–$C_4$ alkyl radical, and a $C_1$–$C_4$ acyl radical;

$RO_1$ is a divalent alkyleneoxy residue;

p is a positive integer; and

RO is a hydrophobic group linked to the alkylene units of the AMP residue.

81. The device or kit according to claim 79, wherein said at least one thickening polymer with an aminoplast-ether skeleton corresponds to the general structure (II):

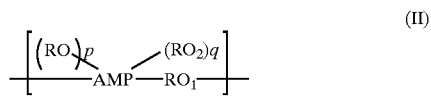

(II)

wherein:

AMP is an aminoplast residue with alkylene units;

R is chosen from a hydrogen atom, a $C_1$–$C_4$ alkyl radical, and a $C_1$–$C_4$ acyl radical;

$RO_1$ is a divalent alkyleneoxy residue;

RO is a hydrophobic group linked to the alkylene units of the AMP residue;

$RO_2$ is a hydrophobic group other than RO linked to the AMP residue via a hetero atom and comprising at least two carbon atoms; and p and q are positive integers.

82. The device or kit according to claim 79, wherein said at least one thickening polymer with an aminoplast-ether skeleton is chosen from structures (III) and (IIIa):

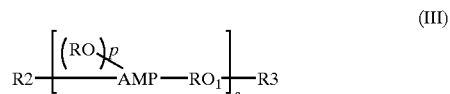

(III)

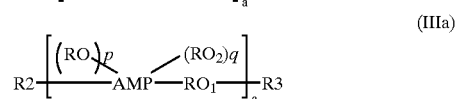

(IIIa)

wherein

AMP is an aminoplast residue with alkylene units;

R is chosen from a hydrogen atom, a $C_1$–$C_4$ alkyl radical, and a $C_1$–$C_4$ acyl radical;

$RO_1$ is a divalent alkyleneoxy residue;

RO is a hydrophobic group linked to the alkylene units of the AMP residue;

$RO_2$ is a hydrophobic group other than RO linked to the AMP residue via a hetero atom and comprising at least two carbon atoms;

p and q are positive integers;

R2 and R3, which may be identical or different, represent an end group chosen from a hydrogen atom, a $RO_1H$ group, a $RO_2H$ group, a AMP(OR)p group and a monofunctional group; and a is a number greater than 1.

* * * * *

UNITED STATES PATENT AND TRADEMARK OFFICE
CERTIFICATE OF CORRECTION

PATENT NO. : 6,984,250 B1
APPLICATION NO. : 10/149008
DATED : January 10, 2006
INVENTOR(S) : Legrand et al.

It is certified that error appears in the above-identified patent and that said Letters Patent is hereby corrected as shown below:

On the cover page,

[*] Notice: Subject to any disclaimer, the term of this patent is extended or adjusted under 35 USC 154(b) by (522) days Delete the phrase "by 522 days" and insert -- by 616 days --

Signed and Sealed this

Nineteenth Day of May, 2009

JOHN DOLL
*Acting Director of the United States Patent and Trademark Office*